United States Patent [19]
Venkatraman et al.

[11] Patent Number: 6,039,977
[45] Date of Patent: Mar. 21, 2000

[54] PHARMACEUTICAL HYDROGEL FORMULATIONS, AND ASSOCIATED DRUG DELIVERY DEVICES AND METHODS

[75] Inventors: Subramanian S. Venkatraman, Palo Alto, Calif.; Thomas O. Murdock, Vadnais Heights, Minn.; Stephanus Pudjijanto, San Jose, Calif.

[73] Assignee: Alza Corporation, Palo Alto, Calif.

[21] Appl. No.: 08/987,372

[22] Filed: Dec. 9, 1997

[51] Int. Cl.[7] .............................. A61K 9/10; A61K 47/32; A61M 37/00
[52] U.S. Cl. .......................... 424/486; 514/944; 424/449
[58] Field of Search .................................. 424/449, 486, 424/452, 455, 433–436, 45, 501; 514/944; 252/315.1; 604/305, 892.1

[56] References Cited

U.S. PATENT DOCUMENTS

| | | | |
|---|---|---|---|
| 4,542,013 | 9/1985 | Keith | 424/28 |
| 4,593,053 | 6/1986 | Jevne et al. | 523/111 |
| 4,781,926 | 11/1988 | Hyon et al. | 424/486 |
| 4,978,531 | 12/1990 | Yamazaki et al. | 424/448 |
| 5,091,185 | 2/1992 | Castillo et al. | 424/438 |
| 5,141,973 | 8/1992 | Kobayashi et al. | |
| 5,346,935 | 9/1994 | Suzuki et al. | 524/18 |

OTHER PUBLICATIONS

Lozinsky, V.I., et al., Journal of Applied Polymer Science, vol. 44, pp. 1423–1435 (1992), "Study of Cryostructurization of Polymer Systems. IX. Poly(Vinyl Alcohol) Cryogels Filled With Particles of Crosslinked Dextran Gel".

Lazzeri, L., et al., Journal of Materials Science: Materials in Mediicine 5 (1994) pp. 862–867, "Physico–chemical and mechanical characterization of hydrogels of poly (vinyl alcohol) and hyaluronic acid".

Lozinsky, V.I., et al., Journal of Applied Polymer science, vol. 58, pp. 171–177 (1995), "Study of Cryostructuration of Polymer systems. XI. The Formation of PVA Cryogels by Freezing–Thawing the Polymer Aqueous Solutions cotnaining Additives of Some Polyols".

Hickey, Alla S., et al., Journal of Membrane Science 107 (1995) pp. 229–237, "Mesh Size and Diffusive Characteristics of Semicrystalline Poly (Vinyl Alcohol) Membranes Prepared by Freezing/Thawing Techniques".

*Primary Examiner*—Edward J. Webman
*Attorney, Agent, or Firm*—Owen J. Bates; D. Byron Miller; Steven F. Stone

[57] ABSTRACT

Pharmaceutical hydrogel formulations containing polyvinyl alcohol are provided. The formulations may serve as rug reservoirs in electrotransport drug delivery systems or passive transdermal systems, or they may be used in a variety of other types of dosage forms, e.g., capsules, suppositories, aerosols, and the like. With these formulations, there is virtually no syneresis encountered upon long term storage, an advantage that derives from selecting the quantity of polyvinyl alcohol in the gel to correspond to the polymer's degree of hydrolysis.

7 Claims, 3 Drawing Sheets

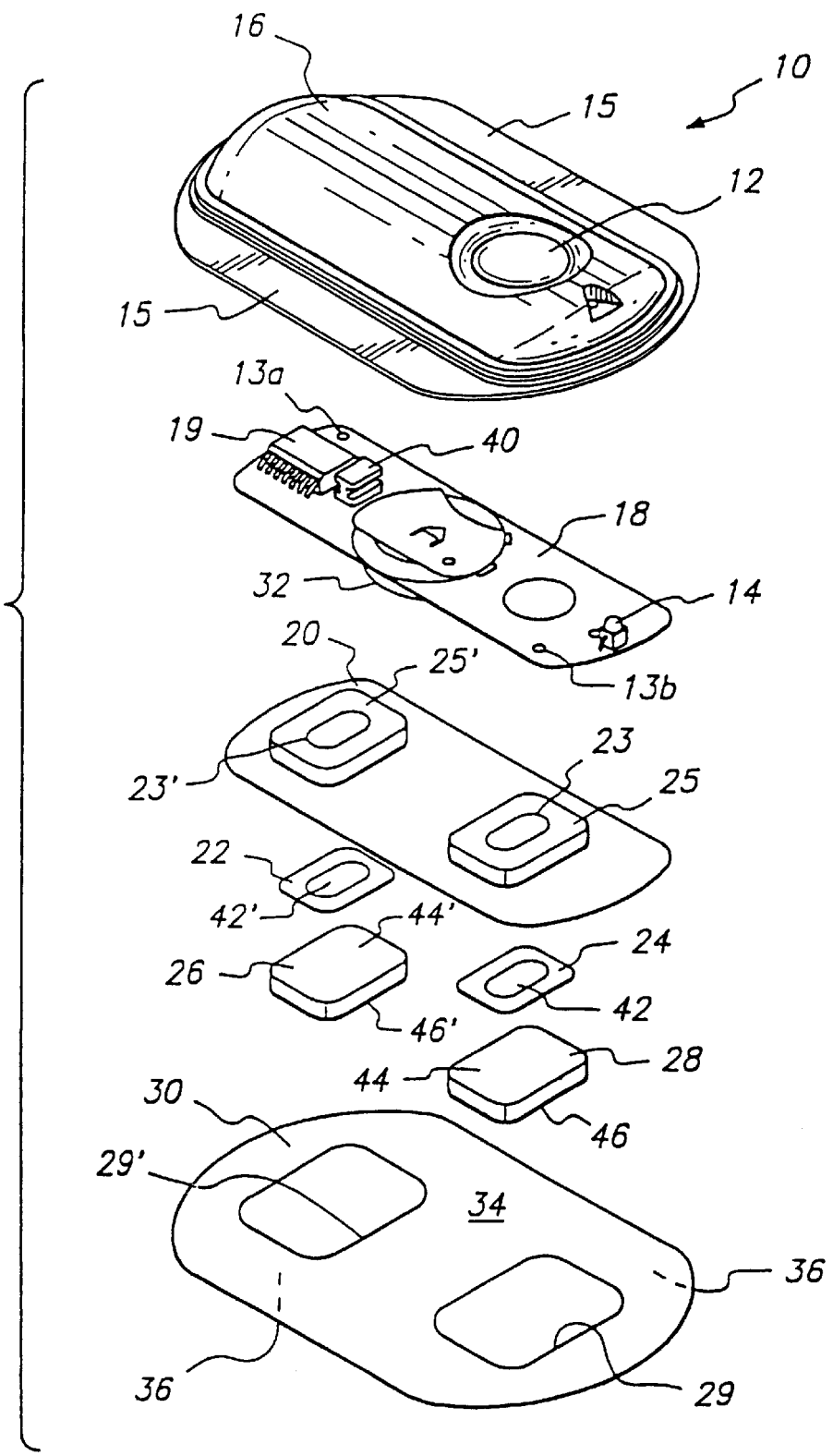

PHARMACEUTICAL HYDROGEL FORMULATIONS, AND ASSOCIATED DRUG DELIVERY DEVICES AND METHODS

TECHNICAL FIELD

This invention relates generally to pharmaceutical formulations. More particularly, the invention relates to pharmaceutical hydrogel formulations which are useful in a variety of contexts, including electrotransport drug delivery. The method also relates to methods for making the formulations and to electrotransport drug delivery systems containing the novel hydrogel formulations as drug reservoirs. The invention further relates to a method for substantially eliminating syneresis in a polyvinyl alcohol system.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of overcoming this limitation in order to achieve transdermal administration of such drugs is the use of electrical current to actively transport drugs into the body through intact skin. The method of the invention relates to such an administration technique, i.e., to "electrotransport" or "iontophoretic" drug delivery.

Herein the terms "electrotransport," "iontophoresis," and "iontophoretic" are used to refer to the transdermal delivery of pharmaceutically active agents by means of an applied electromotive force to an agent-containing reservoir. The agent may be delivered by electromigration, electroporation, electroosmosis or any combination thereof. Electroosmosis has also been referred to as electrohydrokinesis, electroconvection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, the terms "electrotransport", "iontophoresis" and "iontophoretic" refer to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

Systems for delivering ionized drugs through the skin have been known for some time. British Patent Specification No. 410,009 (1934) describes an iontophoretic delivery device which overcame one of the disadvantages of the early devices, namely, the need to immobilize the patient near a source of electric current. The device was made by forming, from the electrodes and the material containing the drug to be delivered, a galvanic cell which itself produced the current necessary for iontophoretic delivery. This device allowed the patient to move around during drug delivery and thus required substantially less interference with the patient's daily activities than previous iontophoretic delivery systems.

In present electrotransport devices, at least two electrodes are used. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to the anode or the cathode of the electrotransport device to provide a fixed or renewable source of one or more desired species or agents.

The present invention is directed in part to a novel drug reservoir for use in an electrotransport system. A preferred material for electrotransport drug reservoirs is polyvinyl alcohol; however, it is well known that hydrogels formed with this polymer are unstable and undergo syneresis, i.e., exude water. This causes the gel to shrink over time with the formation of a separate surface phase, thus diminishing the shelf life of the formulation.

Prior methods for alleviating syneresis have been tried. U.S. Pat. No. 4,593,053 to Jevne et al., for example, calls for a gel composed predominantly of high molecular weight polyvinylpyrrolidone; polyvinyl alcohol is included only as minor component of the gel. However, the use of more than one type of polymer in a hydrogel formulation can have undesirable consequences. For example, nonuniform distribution of a drug within the gel may result if the drug preferentially dissolves in one of the polymers. The optical clarity of the hydrogel may also be compromised. Another approach taken to reduce or eliminate syneresis is to incorporate extraneous moisture-absorbing substances in the formulation, for example, superhygroscopic polymers, synthetic resins, high molecular weight polymeric acids and acid salts, and polyhydric alcohols. See, e.g., U.S. Pat. No. 5,346,935 to Suzuki et al., and U.S. Pat. No. 4,978,531 to Yamazaki et al. Additives and associated impurities which are ionically charged can interfere with electrotransport drug delivery. Additives can also adversely affect the drug release characteristics of the hydrogel itself.

Pharmaceutical polyvinyl alcohol hydrogels that are substantially free of other polymers have also been used in drug delivery systems. For example, an improved flowable gel matrix for transdermal release of trinitroglycerol is described in U.S. Pat. No. 4,542,013 to Keith. The matrix contains two species of polyvinyl alcohol having different molecular weights, and glycerol. The matrix is described as being "less wet" than a commercial sustained release preparation, thus improving the wearability of the transdermal device. U.S. Pat. No. 4,781,926 to Hyon & Ikeda describes a pharmaceutical polyvinyl alcohol hydrogel formulation having a high content of water for the purpose of increasing the swelling of the stratum corneum and thereby enhancing drug permeation through the skin. The gel is prepared by a freeze-thaw process which requires thawing for a period longer than 10 hours to obtain mechanically strong gels. Polyvinyl alcohol has also been used to coat implantable bioactive pellets for veterinary use; see U.S. Pat. No. 5,091,185 to Castillo et al. While these references relate to polyvinyl alcohol hydrogels in the pharmaceutical context, none address the issue of syneresis or provide a way to substantially eliminate the problem of syneresis in pharmaceutical hydrogel formulations comprised of polyvinyl alcohol gels.

To the best of applicants' knowledge, then, the invention represents the first successful attempt to address syneresis in the aforementioned context, and thus provides an important advance in the art by enabling manufacture of stable pharmaceutical hydrogels having a shelf life of at least two years.

SUMMARY OF THE INVENTION

It is a primary object of the invention to provide a pharmaceutical polyvinyl alcohol hydrogel formulation which is stable to syneresis and accordingly can be stored for at least six months at a temperature in the range of 5° C. to 40° C., typically 20° C. to 40° C., with little or no liquid exuding from the gel.

It is another object of the invention to provide such a formulation in the form of a drug reservoir for electrotransport drug delivery.

It is still a further object of the invention to provide such a formulation in the form of a drug reservoir for passive transdermal drug delivery.

It is a further object of the invention to provide an electrotransport drug delivery device containing such a hydrogel drug reservoir.

It is yet a further object of the invention to provide a method for eliminating syneresis in a pharmaceutical polyvinyl alcohol hydrogel formulation, the method involving selecting a degree of hydrolysis and corresponding percent by weight of polyvinyl alcohol in the gel that is effective in forming a hydrogel which is stable to syneresis.

It is still another object of the invention to provide a method for making a pharmaceutical polyvinyl alcohol hydrogel formulation containing a therapeutically effective amount of drug, the method involving preparing an aqueous solution of a known amount of polyvinyl alcohol and a therapeutic amount of drug, freezing the solution, and thawing the frozen solution for a period of no longer than 5 hours. Another object of the invention provides a method suitable for preparing hydrogel formulations containing heat-labile drugs.

Additional objects, advantages and novel features of the invention will be set forth in part in the description which follows, and in part will become apparent to those skilled in the art upon examination of the following, or may be learned by practice of the invention.

In one embodiment of the invention then, a pharmaceutical polyvinyl alcohol hydrogel formulation is provided which is stable to syneresis. The formulation involves the selection of a weight percentage of polyvinyl alcohol in the hydrogel to correspond to the degree of hydrolysis of the polyvinyl alcohol polymer.

A second embodiment of the invention provides a method of making the above formulation. The method entails dissolving a predetermined amount of polyvinyl alcohol in an aqueous liquid, combining the polymer solution with a therapeutically effective amount of drug, and gelling the solution by a freeze-thaw process in which thawing is conducted for a time period of 5 hours or less. The resultant hydrogel is mechanically strong and stable to syneresis. The formulation may be used to form a drug reservoir for passive transdermal drug delivery or for electrotransport drug delivery. Alternatively, the formulation may be combined with a pharmaceutically acceptable carrier suitable for other modes of drug administration. An alternative method for incorporating the drug into the hydrogel involves forming the gel in the absence of drug, removing the water, and hydrating the gel with an aqueous drug solution. This method is particularly useful for drugs and/or formulation additives that are heat-sensitive.

BRIEF DESCRIPTION OF THE DRAWINGS

FIG. 3 is a perspective exploded view of one embodiment of an electrotransport drug delivery system which may be used in conjunction with hydrogels made as described herein.

DETAILED DESCRIPTION OF THE INVENTION

Figure 1:
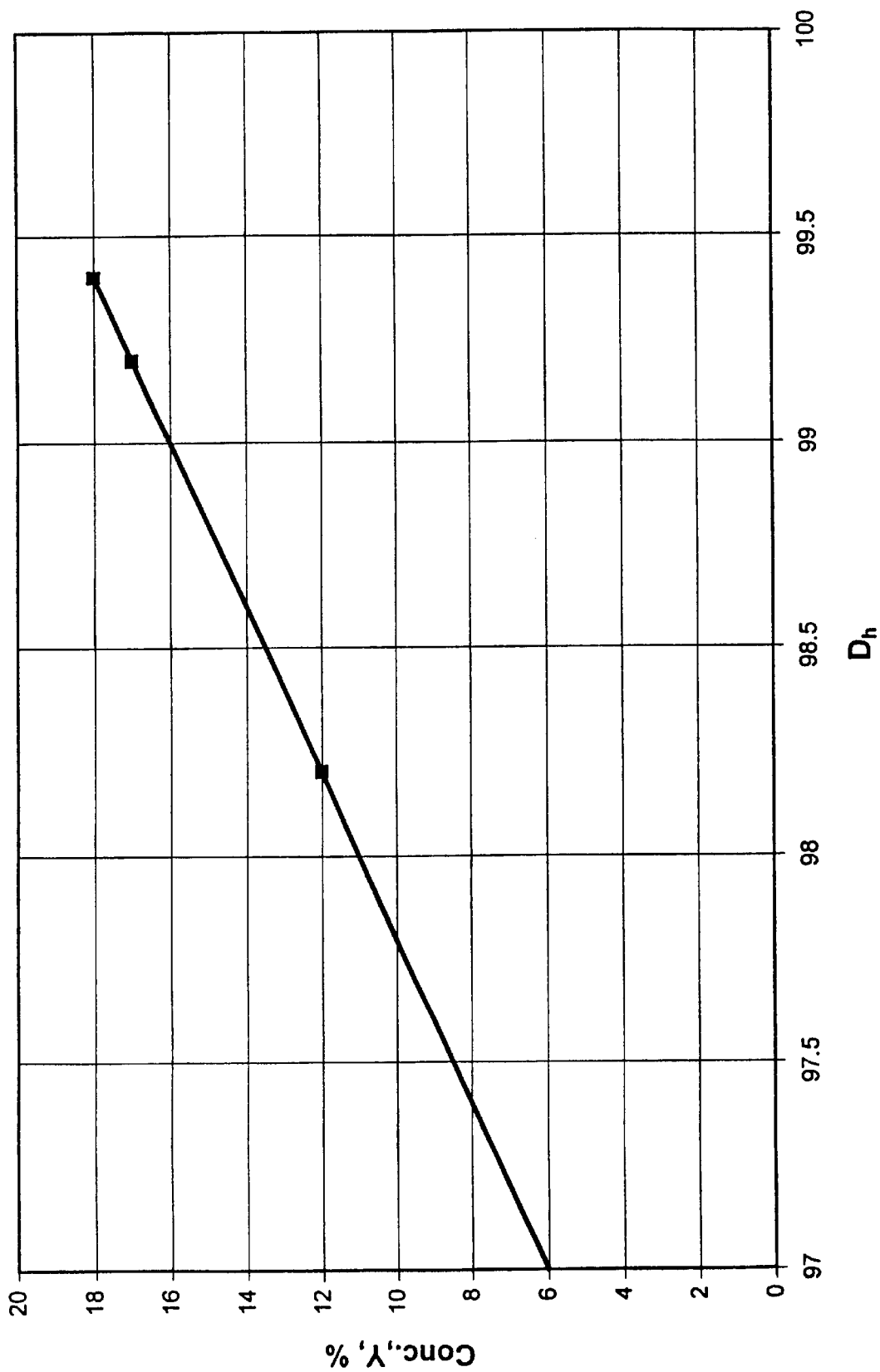
FIG. 1 is a graph illustrating the correlation between the concentration Y of polyvinyl alcohol in a hydrogel with the polymer's degree of hydrolysis $D_h$, for a gel prepared using a single-cycle freeze-thaw procedure.

Before describing the present invention in detail, it is to be understood that this invention unless otherwise indicated is not limited to particular drugs, dosage forms, manufacturing methods, or the like, as such may vary.

It must be noted that, as used in this specification and the appended claims, the singular forms "a," "an" and "the" include plural referents unless the content clearly dictates otherwise. Thus, for example, reference to "a drug" includes a mixture of two or more drugs, reference to "a carrier" includes reference to one or more carriers, and the like.

In describing and claiming the present invention, the following terminology will be used in accordance with the definitions set out below.

By the term "pharmaceutically active agent" or "drug" as used herein is meant any chemical material or compound which induces a desired local or systemic effect, and is capable of being delivered by electrotransport. Examples of such substances will be set forth below.

By the term "hydrogel" as used herein is meant a gel which has taken up water by hydration.

By the term "degree of hydrolysis" as used herein is meant the mole percent of pendant alcohol groups present in polyvinyl alcohol, which is prepared by hydrolysis of pendant acetate groups in a polyvinyl acetate precursor.

By the term "carrier" as used herein is meant a pharmaceutically acceptable vehicle suitable for oral, topical, transdermal, transmucosal, vaginal, rectal, or buccal drug administration, e.g., a capsule, ointment, cream, gel, aerosol, suppository base, or the like. The vehicles are comprised of materials of naturally occurring or synthetic origin that are nontoxic and do not interact with other components of the formulation in a deleterious manner. Carrier materials suitable for use herein include water, silicone, waxes, petroleum jelly, polyethylene glycol, propylene glycol, liposomes, sugars such as mannitol and lactose and a variety of other materials depending, again, on the specific type of formulation used. The term "carrier" or "vehicle" as used herein may also refer to stabilizers, crystallization inhibitors or other types of additives useful for facilitating drug delivery.

By the term "substantially free," as in a polymeric formulation which is "substantially free" of additional polymers, is meant a polymeric formulation which contains less than about 0.1 wt. %, preferably less than about 0.01 wt. %, of polymeric materials other than polyvinyl alcohol, with the possible exception of polymeric buffers that may be used for pH stabilization.

The invention involves in a first embodiment a pharmaceutical hydrogel which is composed predominantly of polyvinyl alcohol polymer and water, and a therapeutically effective amount of a drug. Other additives known to those skilled in the art may be included, for example, solubilizing agents, tissue permeation enhancers, stabilizers, other agents such as antimicrobial, antifungal and anti-inflammatory agents, inhibitors of drug degradation, pH modifiers, and the like. The formulations are substantially free of other polymers known to improve water retention and/or to prevent syneresis. However, it is contemplated that polymeric acids or bases may be added if desired to adjust the pH of the formulation without adversely affecting the properties of the hydrogel.

The pharmaceutical hydrogel formulations of this invention are intended to be used as a drug reservoir in systems for passive transdermal drug delivery and electrotransport drug delivery, or combined with carriers for other routes of drug administration. The novel polyvinyl alcohol hydrogel formulations possess mechanical integrity and stability to degradation and syneresis over prolonged storage periods. A further characteristic of the present formulations is ease of processability using conventional pumping techniques.

In this regard, the requisite physicochemical characteristics of the hydrogel formulations are primarily determined by the viscosity average molecular weight of the polyvinyl alcohol polymer dispersion and the degree of hydrolysis of the polymer. Polyvinyl alcohol with different molecular weight ranges and different degrees of hydrolysis can be purchased from commercial sources. The polyvinyl alcohol used in the pharmaceutical hydrogel formulations of this invention will have a viscosity average molecular weight in the range of approximately 10,000 to 400,000, preferably 12,000 to 200,000, and most preferably 15,000 to 100,000.

In preparing polyvinyl alcohol hydrogels which are stable to syneresis upon prolonged storage (i.e., at least 6 months at a storage temperature in the range of approximately 5° C. to 40° C., typically 20° C. to 40° C.), the percent by weight of polyvinyl alcohol in the hydrogel, Y, is selected to correspond to the degree of hydrolysis of the polymer, $D_h$. When the $D_h$ is in the range of approximately 95% to 99.9%, Y is in the range of approximately 10 wt. % to 30 wt. %. Preferably, $D_h$ is in the range of approximately 96% to 99% and Y is in the range of approximately 12 wt. % to 25 wt. %.

The pharmaceutical hydrogel formulations of this invention may be conveniently prepared by single- or multiple-cycle freeze-thaw procedures. The single cycle procedure is preferred because it can be performed with minimum delay and manipulation and is capable of forming mechanically stable non-syneresing gels. The following method is useful for preparing hydrogel formulations containing heat-stable pharmaceutical agents. An aqueous solution of polyvinyl alcohol is prepared by heating a predetermined amount of the polymer in an aqueous solvent at a temperature greater than 60° C. for a time sufficient to dissolve the polymer, typically 90° C. for 1.5 hours. The polyvinyl alcohol solution is combined with a therapeutically effective amount of drug and other desired additives, and is then frozen at a temperature below 0° C. for a sufficient time to completely freeze the aqueous solution. Typically, freezing is carried out for one to several hours at temperatures in the range of approximately −10° C. to −35° C. The frozen solution can be thawed at approximately 5° C. to 10° C., typically 5° C., for 1 to 5 hours.

Optionally, the freeze thaw cycle may be repeated at least once and as many as 12–15 times or more. The preparation of polyvinyl alcohol gels by free-thaw cycling has been described in, e.g., U.S. Pat. Nos. 4,524,064, 4,664,857 and 4,925,603 to Nambu, U.S. Pat. No. 4,735,097 to Tanabe et al., U.S. Pat. No. 4,808,353 to Nambu et al., U.S. Pat. No. 4,988,771 to Ikeda et al., and U.S. Pat. No. 5,141,973 to Kobayashi et al.

Figure 2:
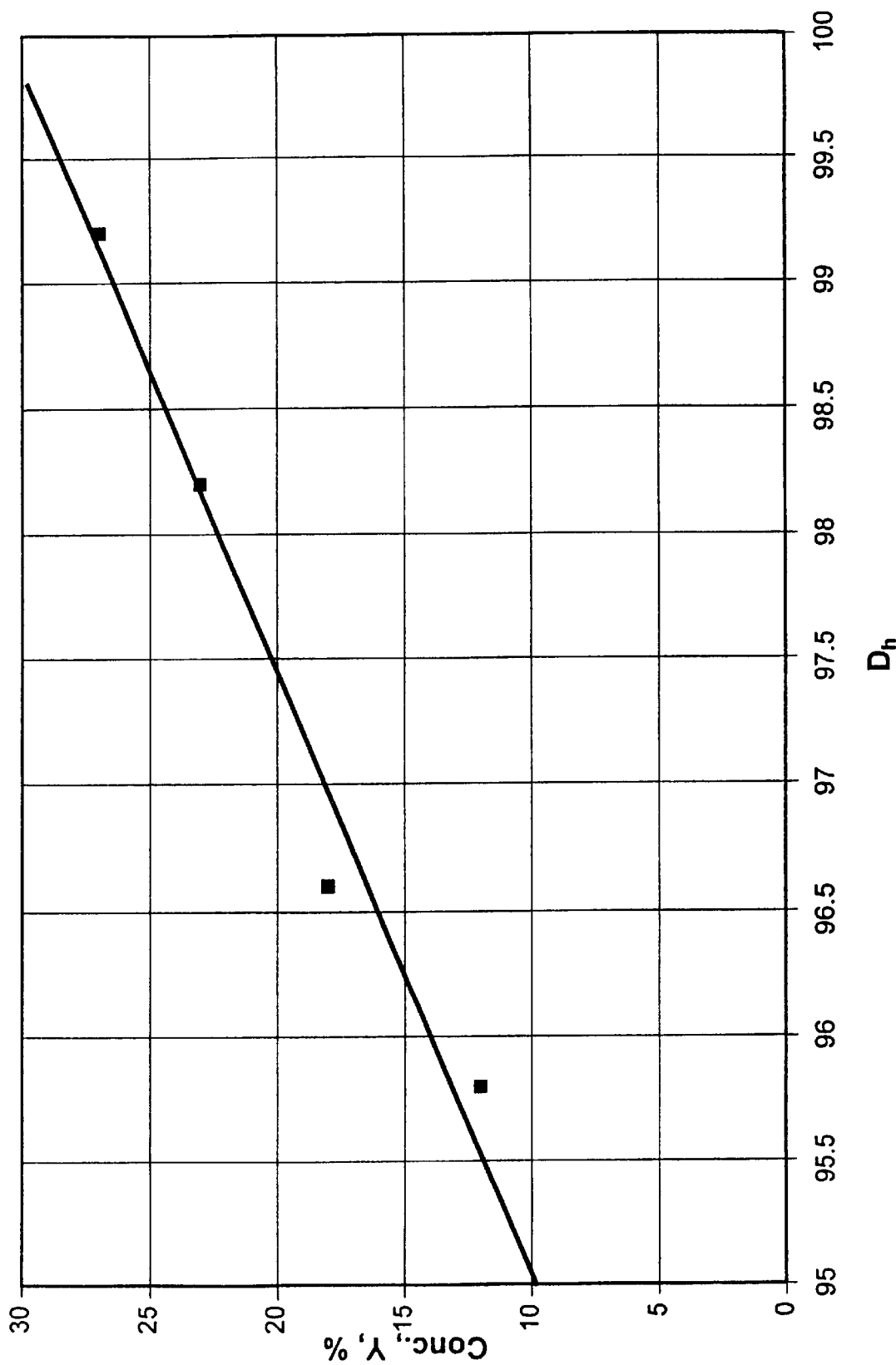
FIG. 2 is a graph illustrating the correlation between the concentration Y of polyvinyl alcohol in a hydrogel with the polymer's degree of hydrolysis $D_h$, for a gel prepared using a multiple-cycle freeze-thaw procedure.

To calculate more specific Y values for any given $D_h$, the number of freeze-thaw cycles involved in preparing the hydrogel needs to be taken account. At higher $D_h$ values, i.e., when working with a degree of hydrolysis greater than about 97.5 wt. %, a single-cycle freeze-thaw procedure is preferred, in which case the concentration Y should be at minimum equal to $5D_h-479$, to provide for an acceptable gel. At lower $D_h$ values, i.e., less than about 97.5 wt. %, multiple-cycle freeze-thaw procedures are preferred (involving at least six and preferably twelve or more cycles), in which case the concentration Y should be at minimum equal to $4.16D_h-385$. The inventors herein have now found that working within these parameters results in gels having good shelf-life and stability, and that working outside of these parameters gives rise to gels that synerese and do not have acceptable shelf-life or stability. The aforementioned relationships are illustrated in the graphs of FIGS. 1 and 2. FIG. 1 pertains to gels prepared using a single-cycle freeze-thaw procedure; FIG. 2 pertains to gels prepared using a multiple-cycle procedure. In each case, for a given $D_h$, the "Y" value should be above the line shown in order to produce a stable gel. Working "below the line" will result in unstable gels which synerese.

The method of the invention may alternatively involve preparing a polyvinyl alcohol hydrogel without the therapeutic agent to be delivered, particularly when a drug or other component of the formulation is heat-sensitive. The hydrogel can be prepared as described above, dehydrated under vacuum, and rehydrated by adding an aqueous solution of the drug and other desired components to the dried hydrogel.

The drug-containing hydrogels can, of course, be dehydrated and stored as dried gels, or diced into portions and rehydrated prior to packaging.

The pharmaceutical hydrogel formulations of the invention are typically used in the form of a drug reservoir in passive transdermal/transmucosal drug delivery or electrotransport drug delivery systems. It will be appreciated by those skilled in the art that the inventive formulations described herein can be combined with suitable carriers to prepare alternative drug dosage forms (e.g., oral capsule, topical ointment, rectal and/or vaginal suppositories, buccal patches, or an aerosol spray).

For oral administration, the hydrogel formulation is preferably encapsulated by a retardant coating, e.g., a bioerodible polymer. Upon dissolution or erosion of the encapsulating material, the hydrogel core becomes exposed and the drug contained within the gel can be released for enteric adsorption. Bioerodible coating materials may be selected from a variety of natural and synthetic polymers, depending on the agent to be coated and the desired release characteristics. Exemplary coating materials include gelatins, carnauba wax, shellacs, ethylcellulose, cellulose acetate phthalate or cellulose acetate butyrate. Release of the agent is controlled by adjusting the thickness and dissolution rate of the polymeric coat.

For topical, transdermal or transmucosal drug administration, the hydrogel is preferably dispersed uniformly in an ointment, gel or cream. Methods for preparing these pharmaceutical compositions are known, or will be apparent, to those skilled in the art. See, e.g., *Remington's Pharmaceutical Sciences*, 18th Ed. (Easton, PA: Mack Publishing Company, 1990).

For vaginal or rectal drug administration, the pharmaceutical hydrogel composition is preferably formulated as a suppository. The suppository can be formed by including the hydrogel formulation in a hollow base core. Both lipophilic and hydrophilic bases may be used, depending on the active agents used in the formulation and the desired drug release profile. The formulation of suppositories suitable for vaginal and/or rectal use is within the general skill of the art.

The pharmaceutical hydrogel formulations of the invention can also be administered as an aerosol. Aerosols for airway diseases are usually administered orally, whereas nasal delivery is preferred for specific nasal problems and for delivery of drugs that are subject to degradation when taken orally.

Microparticles of hydrogel suitable for aerosol administration can also be formed using techniques known to those skilled in the art of pharmaceutical formulation and/or described in the pertinent texts and other literature. See, e.g., *Remington's Pharmaceutical Sciences*, cited above, at Chapter 92 ("Aerosols"). Aerosol formulations will contain the hydrogel microparticles, suitable carriers or excipients, inhalants, and the like, and are typically administered using metered-dosage devices.

Buccal dosage forms of the pharmaceutical hydrogel formulation of the invention are preferred for drugs that are extensively degraded by first-pass metabolism in the liver and for drugs that are susceptible to modification in the low pH environment of the stomach or by enzymes in the gastrointestinal tract (e.g., peptides and proteins). For buccal drug administration, the hydrogel may be incorporated in laminated patches for insertion inside the mouth, in adhesive patches for delivery into the buccal cavity, or may be used in the form of a drug reservoir in a transdermal/transmucosal delivery system such as is described below.

In a passive transdermal/transmucosal drug delivery system, the hydrogel drug reservoir is sandwiched between an upper backing layer and a skin contact adhesive layer in a laminated structure to be affixed to the skin or mucosal surface. The laminated structure may contain a single reservoir, or it may contain multiple reservoirs. The backing layer in these laminates, which serves as the upper surface of the device, functions as the primary structural element of the laminated structure and provides the device with much of its flexibility. The material for the backing material should be selected so that it is substantially impermeable to the drug and to any other components of the drug-containing composition, thus preventing loss of any components through the upper surface of the device. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material. Such devices may be fabricated using conventional techniques, known in the art.

As for other topical formulations of the invention, the drug composition contained within the drug reservoirs of these laminated systems may contain a number of components. Other components which may be present include preservatives, stabilizers, surfactants, and the like.

Both the topical formulations and the laminated drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, dimethylsulfoxide (DMSO), dimethyl formamide (DMF), N,N-dimethylacetamide (DMA), decylmethylsulfoxide ($C_{10}$MSO), $C_2$–$C_6$ alkanediols, and the 1-substituted azacyclo-heptan-2-ones, particularly 1-n-dodecylcyclazacycloheptan-2-one (available under the trademark Azone® from Whitby Research Incorporated, Richmond, Va.), alcohols, and the like.

As noted above, drugs useful in connection with the present invention include any pharmaceutical compound or chemical that is capable of being administered by passive transdermal or transmucosal delivery or by electrotransport. In general, this includes agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathoimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, psychostimulants, sedatives and tranquilizers. The invention is also useful in conjunction with the electrotransport delivery of proteins, peptides and fragments thereof, whether naturally occurring, chemically synthesized or recombinantly produced.

Particular drugs of interest are alniditan ((−)-(R)-[(3,4-dihydro-2H-1-benzopyran-2-yl)methyl]-N'-(1,4,5,6-tetrahydropyrimidinyl)-1,3-propanediamine dihydrochloride) and its analogs, which are useful as antimigraine agents and have been found to be particularly suitable for electrotransport delivery. Further information concerning such agents may be found in PCT Publication No. WO93/17017 (DeBruyn et al.), the disclosure of which is incorporated by reference herein.

As noted hereinabove, the invention is also useful in the controlled delivery of peptides, polypeptides, proteins and other such species. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: [[(s)-4-oxo-2-azetidinyl] carbonyl]-L-histidyl-L-prolinamide), liprecin, pituitary hormones (e.g., HGH, HMG, desmopressin acetate, etc), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSl's , enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Additional agents include fentanyl hydrochloride, pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

Divalent and polyvalent drugs include, but are not limited to, alniditan, discussed above, as well as talipexole dihydrochloride, carpipramine dihydrochloride, histamine dihydrochloride, proflavine dihydrochloride and gusperimus trihydrochloride.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. No. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., the disclosures of which are incorporated by reference herein.

FIG. 3 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in the figure) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and drug/chemical reservoirs 26,28, all of which are integrated into a self-contained unit. The outputs (not shown in the figure) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assure that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The reservoirs 26 and 28 comprise a gel matrix, with at least one of the reservoirs comprised of the hydrogel formulation of the invention. Drug concentrations in the range of approximately $1 \times 10^{-4}$ M to 1.0 M or more can be used, with drug concentrations in the lower portion of the range being preferred.

While the invention has been described in conjunction with the preferred specific embodiments thereof, it is to be understood that the foregoing description as well as the example which follows are intended to illustrate and not limit the scope of the invention. Other aspects, advantages and modifications within the scope of the invention will be apparent to those skilled in the art to which the invention pertains.

EXAMPLE

A. Polyvinyl Alcohol Solution Preparation

Aqueous solutions of 15%, 17% and 20% by weight of polyvinyl alcohol (Mowiol 28–99, obtained from Hoechst-Celanese corporation, Specialty Chemicals Group, Charlotte, N.C.; degree of hydrolysis was 99.2%) were prepared by adding a calculated amount of the dry polyvinyl alcohol powder into a mixing vessel (capacity approximately 100 cm$^3$) and slowly dissolving it in water. The total batch size of each mixture, including water and polyvinyl alcohol, was 70 grams. The vessel was equipped with a lid having a hole to accommodate a stirring shaft. The stirring shaft having a teflon paddle was connected to a motor capable of rotating in the clockwise and counter-clockwise directions at variable speeds. The vessel was jacketed, and silicone oil was circulated through the jacket to control temperature. After adding the polyvinyl alcohol powder and water to the vessel, the lid was applied, the shaft motor was turned on and the heated oil circulation begun. The temperature of the oil was raised to 90° C. with continued stirring of the mixture. After the temperature reached 90° C., mixing was continued for 45 minutes, at which point the mixture was homogenous and clear.

B. Freeze-thaw Curing Cycle

At the end of the mixing procedure described in section A, the solution was cooled to room temperature. It was then transferred to pre-prepared foam cavities for freeze-thaw curing. Each foam cavity had a diameter of 1.9 cm (0.75 inch), a thickness of 1.0 mm (40 mils), and a siliconized polyethylene terephthalate (PET) film cover to prevent contamination and evaporative moisture loss. A typical solution weight ranged between 500 and 600 mg. The solutions were then frozen at −20° C. for 1 hour and thawed at 5° C. for 1 hour, in a Bemco Freezer Oven (Bemco Inc., Simi Valley Calif.). This freeze-thaw cycle was repeated twelve times for certain samples (see FIG. 2). However, for other samples, only a single freeze-thaw cycle was used (see FIG. 1). In the latter case, freeze-thaw conditions were slightly different, the samples being exposed to −20° C. for 12 hours and thawed at room temperature (by removing them from the freezer) for a few hours. Holding samples for an extended time at the freeze temperature did not change the modulus, strength or syneresis characteristics of the gels. This procedure was adopted for convenience in curing a large number of samples.

C. Stability Studies

Each cured gel sample, in its individual foam cavity housing, was weighed at time t=0. These were then aged at different conditions: 25° C. and 40° C., with samples taken at 1 week, 3 weeks, 5 weeks, 10 weeks, 15 weeks and 27 weeks. At each time point, the sample was quickly removed from the foam housing, dried with a wipe and quickly weighed. Each time point involved an average of four sample weighings at each condition. A change in weight was computed from the final and initial weights, as a percentage of the initial weight. For those samples which underwent 12 freeze-thaw cycles, only the 40° C. temperature condition was used for aging.

As a rule, commercial polyvinyl alcohol hydrogels used as drug reservoirs in a drug delivery device should not exhibit a weight loss of greater than 10% after two years at ambient temperature. The two-year shelf-life test is commonly estimated by measuring weight loss over shorter time periods at higher than ambient temperatures. In these tests, the gels prepared as described above were subjected to temperatures of 40° C. for about six months (i.e., 27 weeks) as an estimate of the weight loss that would be seen with similar gels aged for two years at 25° C. For a gel sample to be considered stable over two years at ambient temperature, therefore, the weight loss of gel after six months at 40° C. should be less than 10% by weight. The results obtained are as follows:

| Sample | Wt. Loss, %, N = 1 27 weeks @ 25° C. | Wt. Loss, %, N = 1 27 weeks @ 40° C. | Wt. Los, %, N = 12 27 weeks @ 40° C. |
| --- | --- | --- | --- |
| 15% Mowiol 28-99 | 8.9% Minimal syneresis, translucent | 12.2% Noticeable syneresis, more opaque | 28.8% Significant syneresis, completely opaque |
| 17% Mowiol 28-99 | 3.7% Minimal syneresis, transparent | 8.4% Minimal syneresis, opaque | 23.7% Significant completely opaque |
| 20% Mowiol 28-99 | 5.2% Minimal syneresis, transparent | 8.1% Minimal syneresis, opaque | 20.2% Significant syneresis, completely opaque |

We claim:

1. A method for eliminating or reducing syneresis in a pharmaceutical hydrogel formulation comprised of (a) a therapeutically effective amount of a drug in (b) a hydrogel comprised of water and polyvinyl alcohol having an average viscosity molecular weight between approximately 10,000 and 400,000, wherein the polyvinyl alcohol has a predetermined degree of hydrolysis $D_h$ between approximately 95% and 99% and represents Y percent by weight in a range of approximately 10 wt. % to 30 wt % of the hydrogel, the method comprising a. selecting Y and $D_h$ to correspond to each other such that if $D_h$ is greater than approximately 97.5% then Y is greater than or equal to approximately $5D_h-479$ or if $D_h$ is less than approximately 97.5% then Y is greater than or equal to approximately $4.16D_h-385$;

b. preparing a solution of polyvinyl alcohol having the parameters selected from step a c. subjecting said solution to at least a single-cycle freeze-thaw procedure if Dh is greater than approximately 97.5% or subjecting said solution to a multi-cycle freeze-thaw procedure if Dh is less than approximately 97.5% which provides for a stable hydrogel and reduces or eliminates syneresis upon storage of the formulation for at least six months at a storage temperature in the range of approximately 5° C. to 40° C.

2. The method of claim 1, wherein $D_h$ is in the range of approximately 96% to 99% and Y is in the range of approximately 12 wt. % to 25 wt %.

3. The method of claim 1, wherein syneresis is reduced or eliminated upon storage of the formulation for at least six months at a storage temperature in the range of approximately 20° C. to 40° C.

4. The method of claim 1 wherein the polyvinyl alcohol has a viscosity average molecular weight in the range of approximately 12,000 to 200,000.

5. The method of claim 4, wherein the polyvinyl alcohol has a viscosity average molecular weight in the range of approximately 15,000 to 100,000.

6. A method for eliminating or reducing syneresis in a pharmaceutical hydrogel formulation comprised of (a) a therapeutically effective amount of a drug in (b) a hydrogel comprised of water and polyvinyl alcohol having an average viscosity molecular weight between approximately 10,000 and 400,000, wherein the polyvinyl alcohol has a predetermined degree of hydrolysis $D_h$ between approximately 95% and 99% and represents Y percent by weight in a range of approximately 10 wt. % to 30 wt % of the hydrogel, the method comprising a. selecting Y and $D_h$ to correspond to each other such that $D_h$ is greater than approximately 97.5% and Y is greater than or equal to approximately $5D_h-479$;

b. preparing a solution of polyvinyl alcohol having the parameters selected from step a c. subjecting said solution to at least a single-cycle freeze-thaw procedure, which provides for a stable hydrogel and reduces or eliminates syneresis upon storage of the formulation for at least six months at a storage temperature in the range of approximately 5° C. to 40°.

7. A method for eliminating or reducing syneresis in a pharmaceutical hydrogel formulation comprised of (a) a therapeutically effective amount of a drug in (b) a hydrogel comprised of water and polyvinyl alcohol having an average viscosity molecular weight between approximately 10,000 and 400,000, wherein the polyvinyl alcohol has a predetermined degree of hydrolysis $D_h$ between approximately 95% and 99% and represents Y percent by weight in a range of approximately 10 wt. % to 30 wt % of the hydrogel, the method comprising a. selecting Y and $D_h$ to correspond to each other such that is Y is greater than or equal to approximately $4.16D_h-385$;

b. preparing a solution of polyvinyl alcohol having the parameters selected from step a c. subjecting said solution to a multiple-cycle freeze-thaw procedure, which provides for a stable hydrogel and reduces or eliminates syneresis upon storage of the formulation for at least six months at a storage temperature in the range of approximately 5° C. ot 40°.

* * * * *

US006039977C1

(12) EX PARTE REEXAMINATION CERTIFICATE (5555th)
United States Patent
Venkatraman et al.

(10) Number: US 6,039,977 C1
(45) Certificate Issued: Oct. 10, 2006

(54) PHARMACEUTICAL HYDROGEL FORMULATIONS, AND ASSOCIATED DRUG DELIVERY DEVICES AND METHODS

(75) Inventors: Subramanian S. Venkatraman, Palo Alto, CA (US); Thomas O. Murdock, Vadnais Heights, MN (US); Stephanus Pudjijanto, San Jose, CA (US)

(73) Assignee: Alza Corporation, Palo Alto, CA (US)

Reexamination Request:
No. 90/007,226, Sep. 27, 2004

Reexamination Certificate for:
Patent No.: 6,039,977
Issued: Mar. 21, 2000
Appl. No.: 08/987,372
Filed: Dec. 9, 1997

(51) Int. Cl.
*A61K 9/32* (2006.01)

(52) U.S. Cl. ............... 424/486; 424/449; 514/944
(58) Field of Classification Search ............ 424/486
See application file for complete search history.

(56) References Cited

U.S. PATENT DOCUMENTS

| 4,664,857 A | 5/1987 | Nambu |
| 4,925,603 A | 5/1990 | Nambu |
| 5,260,066 A | 11/1993 | Wood et al. |
| 5,288,503 A | 2/1994 | Wood et al. |

6,650,934 B1   11/2003   Murdock

FOREIGN PATENT DOCUMENTS

| EP | 0516026 A1 | 12/1992 |
| WO | WO 98/08492 | 3/1998 |
| WO | WO 98/26760 | 6/1998 |

OTHER PUBLICATIONS

Encyclopedia of Polymer Science and Engineering, vol. 17, 1989, pp. 167–198.*

Nikolaos A. Peppas and Jill E. Scott, "Controlled Release from Poly (vinyl alcohol) Gets Prepared by Freezing–thawing Processes", 1992, pp. 95–100, 18, *Journal of Controlled Release*.

Nikoloas A. Peppas and Shauna R. Stauffer, "Reinforced Uncrosslinked Poly (Vinyl Alcohol) Gets Produced by Cyclic Freezing–Thawing Processes: a Short Review", 1991, pp. 305–310, 16, *Journal of Controlled Release*.

* cited by examiner

*Primary Examiner*—San-Ming Hui

(57) ABSTRACT

Pharmaceutical hydrogel formulations containing polyvinyl alcohol are provided. The formulations may serve as rug reservoirs in electrotransport drug delivery systems or passive transdermal systems, or they may be used in a variety of other types of dosage forms, e.g., capsules, suppositories, aerosols, and the like. With these formulations, there is virtually no syneresis encountered upon long term storage, an advantage that derives from selecting the quantity of polyvinyl alcohol in the gel to correspond to the polymer's degree of hydrolysis.

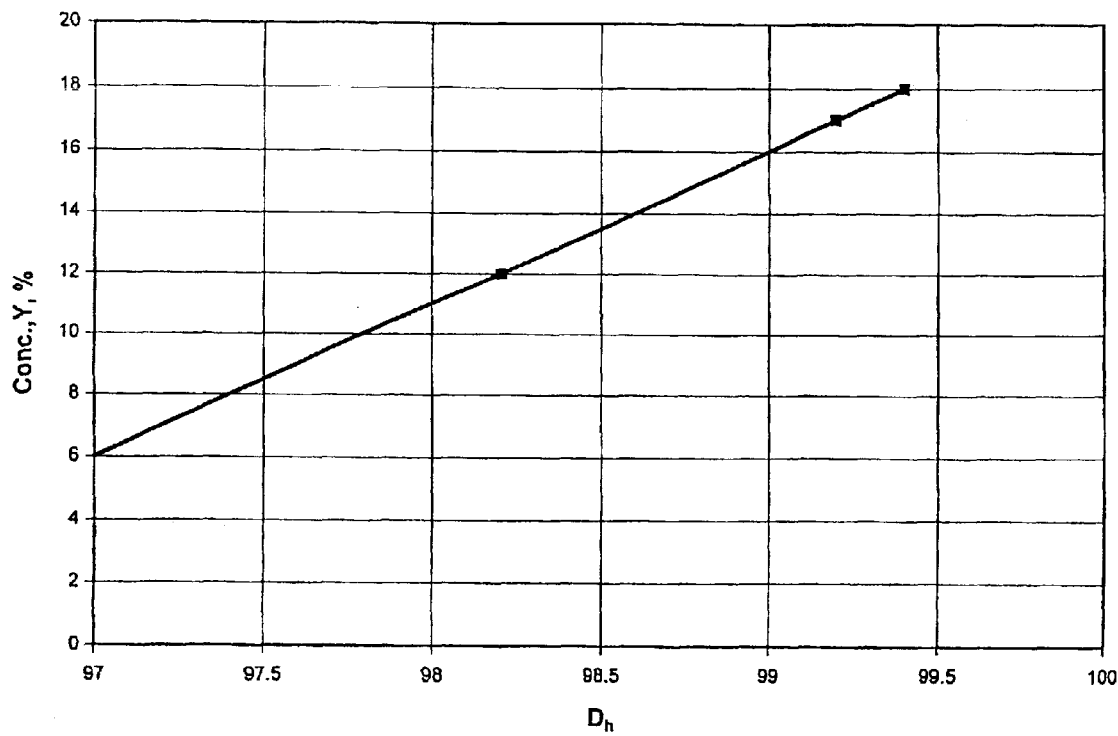

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *